United States Patent [19]
Greene et al.

[11] Patent Number: 5,824,311
[45] Date of Patent: Oct. 20, 1998

[54] TREATMENT OF TUMORS WITH MONOCLONAL ANTIBODIES AGAINST ONCOGENE ANTIGENS

[75] Inventors: Mark I. Greene, Penn Valley, Pa.; Jeffrey A. Drebin, Baltimore, Md.

[73] Assignee: Trustees of The University of Pennsylvania, Philadelphia, Pa.

[21] Appl. No.: 347,019

[22] Filed: Nov. 30, 1994

Related U.S. Application Data

[63] Continuation of Ser. No. 573,527, Aug. 27, 1990, abandoned, which is a continuation-in-part of Ser. No. 126,572, Nov. 30, 1987, abandoned.

[51] Int. Cl.$^6$ ............................ C07K 16/30; C07K 16/28
[52] U.S. Cl. .................................. 424/138.1; 424/143.1; 530/387.7; 530/388.22
[58] Field of Search ........................... 530/387.7, 388.22; 424/138.1, 143.1; 435/240.27, 172.2, 70.214

[56] References Cited

U.S. PATENT DOCUMENTS

| | | | |
|---|---|---|---|
| 4,443,427 | 4/1984 | Reinnerz et al. | 424/1.1 |
| 4,444,744 | 4/1984 | Goldenberg | 424/1.1 |
| 4,454,106 | 6/1984 | Gansow et al. | 424/1.1 |
| 4,522,918 | 6/1985 | Schlom et al. | 435/68 |

OTHER PUBLICATIONS

Bargmann et al., "The neu Oncogene Encodes an Epidermal Growth Factor Receptor–related Protein", Nature vol. 319, pp. 226–230 (1986).
Bast et al., "Elimination of Malignant Clonogenic Cells from Human Bone Marrow Using Multiple Monoclonal Antibodies and Complement" Cancer Research 45: 499–503 (1985).
Bialy, H., "The Ripening Fruits of Receptor Biology" Bio-technology 5: 207 (1987).
Capone et al., "Relationship Between Antigen Density And Immunotherapeutic Response Elicited by Monoclonal Antibodies Against Solid Tumors" JCNI 72: 673–677 (1984).
Ceriani et al., "An Experimental Model for the Immunological Treatment of Breast Cancer" Proc. International Workshop on Molecular Antibodies 248–268 (1984).
Chu, "Potential Applications of Monoclonal Antibodies in Cancer Diagnosis and Therapy" Cancer Investigation 3(6): 565–584 (1985).
Dillman, "Monoclonal Antibodies for Treating Cancer" Annals of Internal Medicine 111: 592–603 (1989).
Drebin et al., "Monoclonal Antibodies Reactive with Distinct Domains of the neu Oncogene–encoded p185 Molecule Exert Synergistic Anti–tumor Effects in Vivo" Oncogene 2: 273–277 (1988).
Drebin et al., "Down–Modulation of an Oncogene Protein Product and Reversion of the Transformed Phenotype by Monoclonal Antibodies" Cell 41: 695–706 (1985).
Drebin et al., "Development of Monoclonal Antibodies Reactive with the Product of the Neu Oncogene " Symposium on Fundamental Cancer Research 38: 277–289 (1986).
Drebin et al., "Monoclonal Antibodies Identify a Cell–Surface Antigen Associated with an Activated Celular Oncogene" Nature 312: 545–548 (1984).
Drebin et al., "Monoclonal Antibodies Specific for the Neu Oncogene Product Directly Mediate Anti–Tumor Effects in Vivo" Oncogene 2: 387–394 (1988).
Drebin et al., "Inhibition of Tumor Growth by a Monoclonal Antibody Reactive with an Oncogene–Encoded Tumor Antigen" PNAS USA 83: 9129–9133 (1986).
Eisenberg et al., "The Helical Hydrophobic Moment: A Measure of The Amphiphilicity of a Helix" Nature 229: 371–374 (1982).
Fendly et al., "Characterization of Murine Monoclonal Antibodies Reactive to Either the Human Epidermal Growth Factor Receptor or HER2/neu Gene Product" Cancer Res. 50: 1550–1558 (1990).
Harris et al., "Therapeutic Antibodies—the Coming of Age" Tibtech 11: 42–44 (1993).
Herbert et al., "Dictionary of Immunology" Blackwell Sci. Publ. p. 120 (1971).
Herlyn et al., Journal of Immunology 134: 1300–1304 (1985).
Hird et al., "Genes & Cancer" Carney et al. Eds., Wiley, pp. 183–189 (1990).
Hung et al., "Molecular Cloning of the Neu Gene: Absence of Gross Structural Alteration in Oncogenic Alleles" PNAS USA 83: 261–264 (1986).
Olsson, L., "Human Monoclonal Antibodies in Experimental Cancer Research" JCNI 75: 397–403 (1985).
Osband et al., "Problems in the Investigational Study and Clinical Use of Cancer Immunotherapy" Immunology Today 11: 193–195 (1990).
Pepys, "Role of Complement in Induction of the Allergic Response" Nature New Biology 237: 157 (1972).
Rose et al., "Hydrophobicity of Amino Acid Residues In Globular Proteins" Science 229: 834–838 (1985).
Schlom "Monoclonal Antibodies: They're More and Less Than You Think" in Molecular Foundations of Oncology, Brode, Ed., Williams and Wilkens pp. 95–134 (1991).

(List continued on next page.)

*Primary Examiner*—Toni R. Scheiner
*Attorney, Agent, or Firm*—Woodcock Washburn Kurtz Mackiewicz & Norris LLP

[57] ABSTRACT

A method of treating certain mammalian tumors with monoclonal antibodies is provided. Monoclonal antibodies specific to distinct epitopes of p185, the translation production of the neu oncongene, are provided, and these are then contacted with the tumor antigen under conditions which allow binding of the antibodies to a degree sufficient to inhibit tumor growth. The monoclonal antibodies act synergistically thus enhancing their anti-tumorigenic effect upon the tumor. An injectable composition for treating certain mammalian tumors with monoclonal antibodies and methods for diagnosing mammalian cancer tumors which express the protein p185 on the surface of the cells are also disclosed.

24 Claims, 2 Drawing Sheets

OTHER PUBLICATIONS

Spiegelman et al., "Molecular Cloning of mRNA from 3T3 Adipocytes" J. Biol Chem. 258: 10083–10089 (1983).

Sugita et al., "Use of a Cocktail of Monoclonal Antibodies and Human Complement in Selective Killing of Acute Lymphocytic Leukemia Cells" Int. J. Cancer 37: 351–357 (1986).

Thiery et al., "Pathways and Mechanisms of Avian Trunk Neural Crest Cell Migration and Localization" Develop Biol. 93: 324–343 (1982).

Trojanowski et al, "A Comparison of Eight Different Chromogen Protocols for the Demonstration of Immunoreactive Neurofilaments or Glial Filaments in Rat Cerebellum Using the Peroxidase–Antiperoxidase Method and Monoclonal Antibodies" J. Histochem. Cytochem. 31: 1217–1223 (1983).

Waldmann, "Monoclonal Antibodies in Diagnosis and Therapy" Science 252: 1657–1662 (1991).

Wawrzynczak et al., "Strategies in Antibody Therapy of Cancer" Clin. Exp. Immuol. 82: 189–193 (1990).

Yung and Cudkowicz, "Abrogation of Resistance to Foreign Bone Marrow Grafts by Carageenans II. Studies with the Anti–Macrophage Agents" J. Immunology 119: 1310 (1977).

Drebin et al., "In Vivo and In Vitro Effects of Monoclonal Antibodies which Recognize a Cell Surface Oncogene Product" J. Cell Biochem. 0(9 Part A) p. 72 ( Abstract #0170) (1985).

Wada, T. et al., "Intermolecular Association of the $p185^{neu}$ Protein and EGF Receptor Modulates EGF Receptor Function" Cell 61: 1339–1347 (1990).

Qian et al., "$p185^{c-neu}$ and epidermal growth factor receptor associate into a structure composed of activated kinases" PNAS USA 89: 1330–1334 (1992).

Mattern et al., "Human Tumor Xenografts as Model for Drug Testing" Cancer and Metastasis Reviews 7: 263–284 (1988).

Waldmann, "The Interleukin–2 Receptor: A Target for Immunotherapy of Leukemia/Lymphoma" J. Cell. Biochem. Supp 18D #R008 p. 100 (1994).

Hynes et al., "Recombinant Single Chain Immunotoxins Specific for EGF & ERBB–2 Receptors Inhibit in Vivo and in Vitro Tumor Cell Growth" J. Cell. Biochem. Supp 18D: #Y208 p. 237 (1994).

Dougall et al., "Modulation of $p185^{c-erb-2}$ Expression and Tumorigenic Growth by Anti–Receptor Monoclonal Antibodies" J. Cell. Biochem. Supp 18D #Y507 p. 252 (1994).

Houghton et al., "Monoclonal Antibodies: Potential Applications to the Treatment of Cancer" Seminars in Oncology 13: 165–179 (1986).

Bookman et al., "Immunotoxins Directed Against c–erbB2: Limited Activity Due to Poor Internalization" Third International Symposium on Immunotoxins p. 15 (1992).

Wright et al., "Expression of c–erbB–2 Oncoprotein: A Prognostic Indicator in Human Breast Cancer" Cancer Res. 49: 2087–2090 (1989).

Zee–Cheng and Cheng, "Screening and Evaluation of Anticancer Agents" Meth and Find. Exptl. Clin Pharmacol 10(2) 67–101 (1988).

Horak, Eva et al., "Radioimmunotherapy of Nude Mice Bearing a Human Her2/Neu Positive Tumor Utilizing the α–emitting Radionuclide–Conjugated Monoclonal Antibody $^{212}$Pb–Dota–Ae1" Abstract #Y 509 from Breast and Prostate Cancer II, p. 252.

Seaver, Genetic Engineering News vol.14:10,21, 1994.

Wawrzynczak et al., Clin Exp. Immunol.82; 189–193, 1990.

Dillman et al. J.Clinical Oncology 12:1497–1515 1994.

TREATMENT OF TUMORS WITH MONOCLONAL ANTIBODIES AGAINST ONCOGENE ANTIGENS

REFERENCE TO RELATED APPLICATIONS

This is a continuation of application Ser. No. 07/573,527, filed Aug. 27, 1990, now abandoned, which is a continuation-in-part of application Ser. No. 07/126,572, filed Nov. 30, 1987, now abandoned.

FIELD OF THE INVENTION

This invention is directed to treatments and diagnoses for mammalian tumors. More particularly this invention is directed to methods of treating and diagnosing mammalian cancer tumors that employ antibodies.

BACKGROUND OF THE INVENTION

Huge amounts of time and money have been spent searching for mammalian cancer tumor treatments. Current tumor treatments rely on the cytotoxic effects of drugs and radiological therapy. Although these treatments bring remission and cure to some patients, they unfortunately have serious side effects because they kill not only tumor cells but also normal non-tumorous cells. There exists a great need for mammalian tumor treatments which affect only the tumor cells.

Tumor treatments employing immunotherapy by passive transfer of monoclonal antibodies, lymphokines, and/or cellular effectors into the tumor-bearing host has shown promise in laboratory and clinical trials. Most studies of monoclonal antibody-mediated immunotherapy have utilized monoclonal antibodies generated against random structures on the malignant cell surface, and have depended upon the ability of immunologic effector mechanisms in the tumor bearing host to eradicate antibody-coated tumor cells.

U.S. Pat. No. 4,522,918 to Schlom et al. discloses a cancer treatment using monoclonal antibodies directed at surface antigens of human mammary adenocarcinoma cells. These antibodies are activated only by tumor cells from human mammary cells and not by apparently normal human tissues. They were prepared from mouse spleen cells which had been immunized with human metastatic mammary carcinoma cells. The mouse spleens were fused with NS-1 myeloma cells to generate hybridoma culture which secreted antibodies reactive with surface antigens of human mammary adenocarcinoma cells but not with surface antigens of normal cells.

U.S. Pat. No. 4,444,744 to Goldenberg discloses radiolabeled monoclonal antibodies to tumor cell surface antigens to locate, diagnose and stage tumors having such antigens of their cell surfaces. Radiolabeled monoclonal antibodies to a tumor-associated or tumor-specific antigen is injected parenterally into a human subject along with an indifferent immunoglobulin from the same or different species as that used to prepare the specific antibody. The specific and indifferent antibodies are labeled with different isotopes. The level of activity of the labeled indifferent immunoglobulin being used to determine the distribution of background activity due to non-targeted specific antibody, the background activity being subtracted from the total activity of specific antibody, whereby the activity of substantially only the targeted tumor-localized specific antibody is determined and the tumor is thereby detected and localize U.S. Patent to Gansow et al. discloses the use of metal chelate conjugated monoclonal antibodies to diagnose and treat cancer cells. Here monoclonal antibodies specific for a cell or antigen on the cell surface are chelated with a metal which may be radioactive, exhibit fluorogenic properties, exhibit paramagnetic properties or other property. The antibody-metal chelates are injected into to body where they attach to the target cells and kill them or tag the cells so they can be picked up in diagnostic tests.

Capone et al., JNCI 72: 673–677, (1984), investigated the relationship between antigen density and immunotherapeutic response elicited by monoclonal antibodies against solid tumors. These investigators used monoclonal antibodies specific against human breast cancer. It was found that passively administered monoclonal antibody can be effective in producing a tumor regression response against solid tumors. Tumoricidal response with monoclonal antibody appeared to be exponentially related to the density of the antigen on the cells.

In an effort to achieve more potent anti-tumor effects, scientists have begun producing antibodies which are specific for structures necessary for neoplastic cell growth and/or which are capable of directly interfering with neoplastic cell functions. U.S. Pat. No. 4,443,427 to Reinnerz et al. discloses a monoclonal antibody specific to a mature human T cell surface antigen. These monoclonal antibodies are capable of selectively binding mature human T cells and rendering them inactive in vivo and failing to induce the proliferation or activation of human lymphocytes.

Bast et al., Cancer Research 45: 499–503, (1985), studied the in vitro elimination of malignant clonogenic cells from human bone marrow using multiple monoclonal antibodies and complement. These researchers used monoclonal antibodies which react with acute lymphoblastic leukemia cells and in addition to testing each monoclonal antibody singly for antitumorigenic effect, they tested combinations of these monoclonal antibodies. Several combinations of antibodies were found to be more effective than single antibodies; however, a combination of three antibodies was not significantly more effective than the optimal combinations of two antibodies for eliminating tumor cells.

Herlyn et al., Journal of Immunology 134: 1300–1304, (1985), investigated the effects of mixtures of monoclonal antibodies on tumor growth in vitro and in vivo. Some monoclonal antibodies they tested exerted no tumoricidal effect in vitro when used singly, however, two mixtures (two antibodies in each mixture) which were not tumoricidal separately were effective in lysing melanoma cells in vitro when used together. These mixtures of monoclonal antibodies did not, however, affect the growth of these tumors in vivo. Two of the antibodies used by Herlyn et al. bound to different epitopes of the p97 antigen on the melanoma cells. However, when tested as a mixture, they did not act synergistically to reduce tumor growth. They attributed this lack of synergistic effect to stearic hindrance of binding of effector cells to antibody molecules bound to the same antigen. In another study, Ralph and Nakoinz, J. Leuk. Biol. 35: 131, (1984), reported that mixtures of monoclonal antibodies binding to different molecules on the tumor cells surface cooperated in the tumor cell lysis, whereas monoclonal antibodies binding to the same molecule did not.

Thus there is a long-felt need for improved treatments for cancer which affect only the tumor cells. Known treatments have proved to be ineffective in treating cancer tumors in vivo.

Malignant cells display a variety of in vitro characteristics that distinguish them from normal cells. These characteristics, collectively known as the transformed phenotype, include anchorage-independent growth, decreased serum requirements, rounded cellular morphology, increased hexose uptake, loss of microfilaments, increased plasminogen activator secretion, decreased cell surface fibronectin, and increased sensitivity to the drug ouabain. Anchorage-independent growth, as determined by the formation of colonies in soft agar, is the most reliable parameter of the transformed phenotype because it is the phenotypic property most tightly linked with tumorigenic behavior in vivo.

Recent studies in the molecular genetics of cancer indicate that certain genes known as oncogenes may play a role in the transformation of some cells from their normal condition to a cancerous condition. Proto-oncogenes, genes closely related to these genes, are found in somatic cells of all eukaryotic species examined and have been highly conserved in evolution; it is thought that proto-oncogenes normally play critical roles in cellular growth and development. Oncogene amplification and chromosomal rearrangements involving oncogenes have been detected in a large number of tumors. Furthermore some tumors have been shown to contain activated oncogenes which, in DNA transfection assays, are capable of conferring neoplastic properties upon non-neoplastic rodent fibroblast cell lines. Collectively these studies suggest that alterations in proto-oncogene structure and function play a critical role in the development of neoplasia.

Although most oncogene-encoded proteins reside in the nucleus or the cytoplasm, some oncogenes encode proteins that express antigenic sites on the cell surface. For example, the erbB, fms and ros oncogene products are transmembrane glycoproteins that possess extracellular domains. The sis oncogene product may also exist in a membrane associated form on the surface of transformed cells. Another oncogene which encodes a protein that exposes antigenic sites on the surface of transformed cells has been identified by transfection of DNA from ethyl nitrosourea-induced rat neuroblastomas into NIH3T3 cells. This oncogene has been termed neu. The neu gene has been found to be amplified in some human tumors, particularly those of the breast, suggesting that this gene may play a role in the etiology of human cancer.

The neu oncogene encodes a cell surface protein on rat cells transformed by it. The protein encoded by the neu oncogene is a 185 kDa transmembrane glycoprotein with tyrosine kinase activity, generally known by the name p185. The neu gene is closely related to the epidermal growth factor (EGF) receptor gene in structure. It is thought that p185 is a receptor for an, as yet, unidentified growth factor.

The neu oncogene and p185 have also been found active in human adenocarcinomas including breast, lung, salivary gland and kidney adenocarcinomas, as well as prostate neuroblastoma.

In human primary breast cancers amplification of the neu oncogene was found in about 30% of all malignant tumors examined. Increased stage of malignancy, characterized by large tumor size and increased number of positive lymph nodes as well as reduced survival time and decreased time to relapse, was directly correlated with an increased level of amplification of the neu gene. The neu protooncogene is expressed at low levels in normal human tissues.

SUMMARY OF THE INVENTION

The present invention provides methods for the treatment of mammalian cancer tumors having cells which express a translation product of the neu oncogene on their surfaces. In accordance with the invention, a first antibody specific for a first epitope of the translation product and a second antibody specific for a second epitope of the translation product, the combination of first and second antibodies being selected to produce synergistic inhibition of tumor growth, are contacted with the cells under conditions which allow the antibodies to bind to the translation product on the surfaces of the cells to a degree sufficient to inhibit growth of the tumor. In accordance with preferred embodiments of the invention, the translation product of the neu oncogene is p185, a transmembrane glycoprotein having tyrosine kinase activity and a molecular weight of about 185,000 daltons as determined by carrying out electrophoresis on the glycoprotein and comparing its movement with marker proteins of known molecular weight. The exact mechanism of the antitumorigenic effect is not known. Experiments have shown that antibody binding to p185 leads to a reversion of the cancerous phenotype to the non-cancerous phenotype. Anti-p185 antibodies selectively inhibit the neo-plastic behavior of neu transformed cells, without in any way affecting cell viability.

Treatment of tumors with antibodies has been done by others; however, these treatments used monoclonal antibodies singly or in combination with a cytotoxic agent. The present invention shows that antibodies specific for a cell surface structure necessary for malignant cell growth can be curative in vivo. In no studies done previously were antibodies used that interacted with elements necessary for growth. The present invention employs two or more monoclonal antibodies to distinct domains of the same tumor antigen. These antibodies bind to the protein and the effect produced by the antibodies is synergistic. The proper combination of antibodies produces antitumorigenic effects beyond that expected by the mere binding of two antibodies to the tumor antigen. The extent of the tumorigenic effect produced by the proper combination was quite unexpected and could not be anticipated. A few researchers have used mixtures of antibodies to tumor antigens to attempt to reduce tumor size but they were not successful in producing these effects in vivo and the mixtures of antibodies did not act synergistically. Ralph and Nakoinz have succeeded in showing cooperation between monoclonal antibodies binding to different molecules of the tumor cell surface to lyse tumor cells in vitro. These researchers could not show cooperation between antibodies when they used mixtures of antibodies specific for the same molecule. This may relate to the fact that the tumor antigens in question are not intimately involved in malignant cell growth. The antigens studied to date may be expressed as a consequence of malignancy, but do not determine malignant growth. The neu oncogene product specifically and uniquely determines malignant growth on its own.

Accordingly, the invention provides a finely tuned treatment for those mammalian tumors which express the tumor antigen, p185, on their cell surfaces. This treatment is an improvement over tumor treatments already in use because the antibodies affect only tumor cells, unlike mammalian cancer tumor treatments currently in use which affect all cells. The treatment of the invention can thus be expected to reduce or eliminate the serious side effects of mammalian cancer tumor treatments because it does not interfere with any part of the body except the tumor. The invention also provides monoclonal antibodies for the treatment of mammalian cancer tumors that express products of the neu oncogene on their surfaces.

The invention further provides an injectable composition for treatment of a mammalian cancer tumor having cells which express a translation product of the neu oncogene on the surfaces of the cells. In accordance with the invention, the composition comprises a first antibody specific to a first epitope of a translation product, a second antibody specific to a second epitope of a translation product, the combination of first and second antibodies being selected to produce synergistic inhibition of tumor growth, and a pharmaceutically acceptable injection vehicle.

The invention additionally provides methods for diagnosing mammalian cancer tumors which express the protein p185, a translation product of the neu oncogene on the tumor cell surfaces. In accordance with one embodiment of the invention, tumors can be diagnosed by contacting tissue portions of the tumor with an antibody specific for a translation product of the neu oncogene, the antibody being labeled with an indicator. The antibody binds to a translation product of the neu oncogene present in the cells of the tissue portion. The indicator is then detected. In preferred embodiments of the invention, the indicator comprises biotinylated horse anti-mouse immunoglobulin and streptavidin-biotinylated-peroxidase. The indicator is detected by contacting the indicator with a chromogenic substrate which preferably comprises 3,3'-diaminobenzidine, hydrogen peroxide and imidazole. The chromogenic substrate is then detected by microscopy.

In accordance with another embodiment of the invention, a mammalian cancer tumor having cells which express a translation product of the neu oncogene on the surfaces of the cells can be diagnosed by contacting a radiolabeled nucleic acid probe with nucleic acid prepared from the tumor causing the probe to bind to nucleic acid coding for the neu oncogene translation product and detecting the radiolabeled probe. In preferred embodiments of the invention, the radiolabeled probe comprises a nucleic acid fragment of neu oncogene and a radiolabel. The radiolabeled probe is contacted with RNA prepared from the tumor cells and the radiolabeled probe is then detected autoradiographically.

DETAILED DESCRIPTION OF THE INVENTION

Figure 1A:
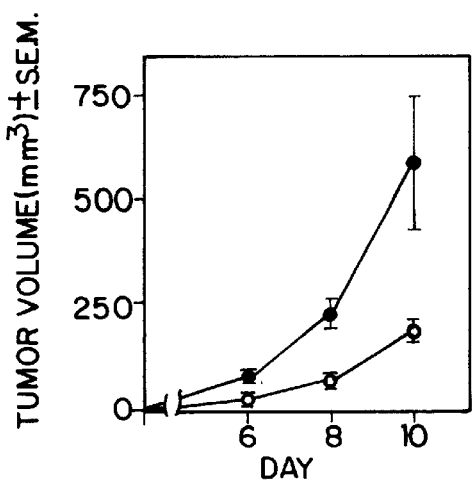
FIG. 1 shows the inhibition of tumorigenic growth of neu-transformed cells after intravenous administration of anti-p185 monoclonal antibodies.
Figure 1B:
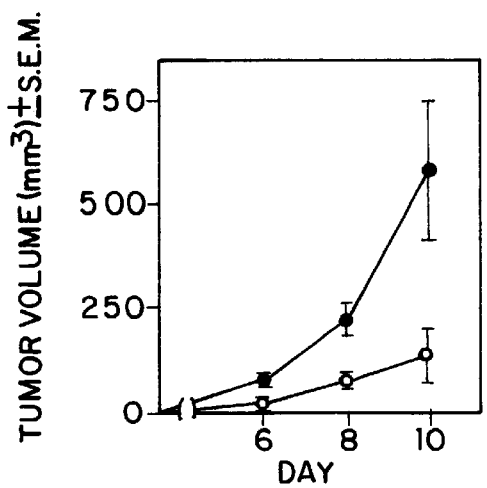
Figure 1C:
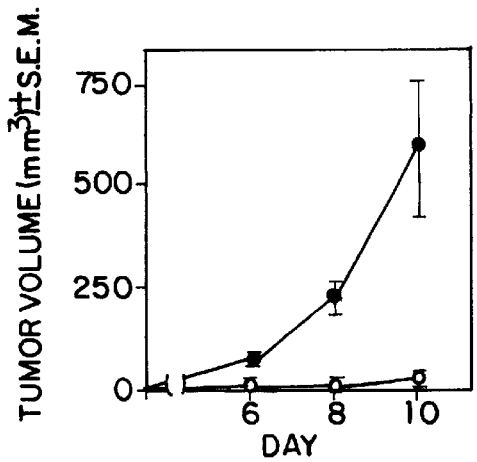
Figure 1D:
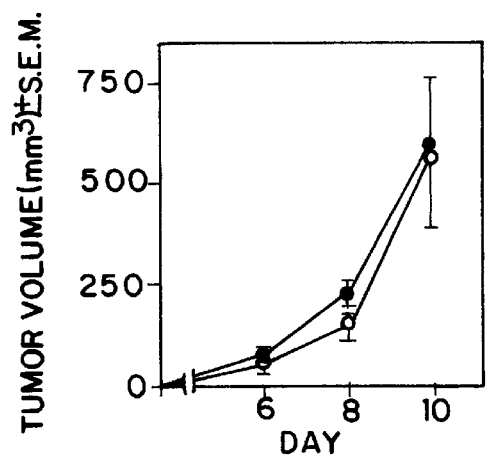
Figure 1E:
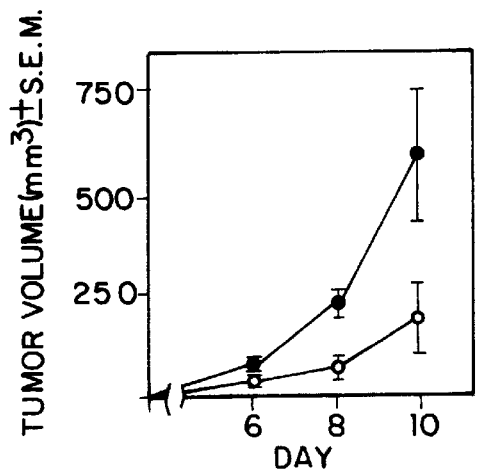
Figure 1F:
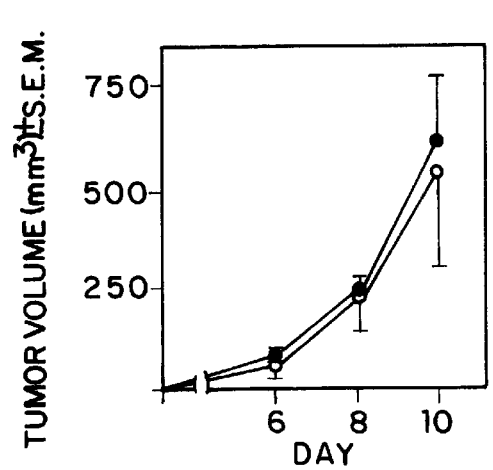

The injectable composition for treatment of mammalian cancer tumors which express p185 on the surface of the cells comprises a mixture of antibodies specific for different domains or sites on the p185 molecule and a pharmaceutically acceptable injection vehicle. The antibodies are chosen from antibodies made according to the procedures described in detail below or other conventional methods for producing monoclonal antibodies. The injection vehicle can be an injection vehicle known in the art such as sterile saline.

Mammalian cancer tumors which express p185 on the surface of the cells can be diagnosed using immunohistochemical and nucleic acid probe/autoradiographical procedures. A detailed description of the preferred embodiments of these procedures is set forth below.

A detailed description of the preferred embodiments of the invention is set forth below.

Experimental

Antibodies specific for different sites of p185.

Transformed Cell Lines

B104-1-1 is a neu oncogene transformed NIH3T3 cell line derived by passing rat neuroblastoma transforming DNA sequences through two cycles of transfection in NIH3T3 cells. XHT-1-1a is a Ha-ras-transformed NIH3T3 cell line. Cells are cultured in 100 mm tissue culture dishes (Costar), in 10 ml of Dulbecco's Modified Eagle's Medium (DMEM, K.C. Biologicals) supplemented with 10% fetal calf serum, 1% pen-strep-fungizone mixture (M.A. Bioproducts) and 100 ug/ml gentamicin sulfate (M.A. Bioproducts). Cell cultures are maintained in a humidified 5% CO2 incubator at 37 C. and replaced from stock every 2–3 months.

Experimental Animals

C3H and [C3H×DBA/2] F1 (C3D2 F1) mice were obtained from the Jackson Laboratory, Bar Harbor, Me. Inbred congenitally athymic Balb/c nude (nu/nu) mice were obtained from the National Cancer Institute animal colony (San Diego, Calif.). Animals used in the experiments are maintained in accordance with the guidelines of the Committee on Care and Use of Laboratory Animals of the Institute of Animal Resources, National Research Council (DHEW publication number (NIH) 78-23, revised 1978).

Isolation of Hybridomas Secreting Monoclonal Antibodies Reactive with Neu-Transformed Cells C3H/HeJ mice are repeatedly immunized with NIH 3T3 transfectants transformed by the neu oncogene (cell line B104-1-1), emulsified in Freund's adjuvant. Spleens from immune mice are fused with the aminopterin-sensitive NS-1 myeloma line, and hybridomas are selected in hypoxanthine-aminopterin-thymidine media. Culture supernatants from growing hybridomas are initially screened for the presence of antibody capable of binding B104-1-1 cells by indirect immunofluorescence using fluorescence activated cell sorting (FACS). Positive supernatants are then tested for specificity by determining whether they contain antibody capable of binding normal NIH 3T3 cells, or NIH 3T3 cells transformed by transfection with Harvey sarcoma virus proviral DNA (cell line XHT-1-1a).

Isotype Analysis of Monoclonal Antibodies

The heavy chain isotypes of the monoclonal antibodies characterized here are determined by double immunodiffusion in agar according to the method of Ouchterlony, in Hudson, L and F. C. Hay, eds., *Practical Immunology*, Blackwell Scientific Publications, London, p. 117, which is specifically incorporated herein.

Purification of Monoclonal Antibodies

Hybridoma cells are washed several times in HBSS and injected into pristine primed, 400 rad irradiated, C3D2F1 mice to induce ascites fluid production. When the mice develop significant ascites, the fluid is removed by aspiration with a 19 gauge needle and hybridoma cells and debris are removed by centrifugation at 1000×g. The clarified ascites fluid is then stored at −70 C. prior to purification, or is purified immediately. Purification is performed according to the method of Drebin et al. in *Immunology and Cancer* (M. L. Kripke and P. Frost, eds.) University of Texas Press, Austin, Tex., p. 277 which is specifically incorporated herein.

II. Specificity of Antibodies Flow Cytometry

Cells are removed from dishes with buffered EDTA (Versene; Gibco) and washed twice in FACS medium (Hank's balanced salt solution (HBBS; Gibco) supplemented with 2% fetal calf serum (FCS), 0.1% sodium azide and 10 mM HEPES); 1×10⁶ cells in 0.1 ml FACS medium are incubated with 0.1 ml of hybridoma culture supernatant for 1 hr at 4 C. Cells are washed twice with FACS medium, and incubated with 0.1 ml fluorescein isothiocyanate (FITC)-conjugated rabbit-anti-mouse immunoglobulin (Miles) diluted 1:50 in FACS medium for 1 hr at 4 C. Cells are then washed twice in FACS medium and fixed in 2% paraformaldehyde-phosphate-buffered saline (PBS). Samples are run on an Ortho 2150 Cytofluorograph using the logarithmic amplifier. Each sample contains 10,000 cells per sample.

Cyanogen Bromide Coupling of Antibodies to Sepharose Beads

CNBr-activated Sepharose 4B beads are swollen in 1 mM HCl, and then mixed with purified antibodies in coupling buffer (0.5M NaCl, 0.1M NaHCO$_3$, pH 8.3) at a ratio of 2 mg immunoglobulin (1 mg per ml) per ml of activated beads. The mixture is rotated overnight on an end-over-end mixture at 4 C., and then unreacted sites are blocked with 0.2M glycine pH 8.0 for 2 hours at room temperature. The beads are then poured onto a sintered glass filter and washed with three cycles of 100 bead volumes of coupling buffer, 10 bead volumes of 3.5M MgCl$_2$, 100 bead volumes of coupling buffer to wash away excess adsorbed proteins. Non-specific protein binding to the antibody coupled beads is blocked by a brief wash in sterile DMEM containing 10% fetal calf serum. The beads are then washed in PBS and stored in PBS containing 0.1% sodium azide at 4 C. until they are used in immunoprecipitation experiments.

All of the monoclonal antibodies which specifically bind to the surface of neu-transformed cells are reactive with the p-185 molecule encoded by the neu oncogene. These monoclonal antibodies specifically precipitate p185 from metabolically labeled lysates of neu-transformed cells.

Immunoprecipitation of p185 from Metabolically Labeled B104-1-1 Cell Lysates For labeling with $^{35}$S-cysteine 10⁶ cells are seeded in 100 mm culture dishes and labelled for 18 hr in 2 ml minimal essential medium (MEM) containing 0.1 the usual amount of cysteine, 2% dialyzed fetal calf serum and 500 uCi $^{35}$S-cysteine (77 Ci mmol$^{-1}$; NEN). For labeling with $^{32}$P, 3×10⁵ cells are seeded in 60-mm tissues culture dishes and incubated for 18 hr in 0.8 ml phosphate-free Dulbecco-Vogt modified Eagle's medium containing 4% fetal calf serum and 0.4 mCi $^{32}$P (carrier-free; NEN). Cells are lysed in phosphate-buffered RIPA buffer containing 1 mM ATP, 2 mM EDTA and 20 mM sodium fluoride, and immunoprecipitates are prepared and washed according to Sefton et al. Virology 28: 957–971 (1979), which is specifically incorporated herein. One third of each lysate is incubated with 1 ul of normal mouse serum or 60× concentrated 7.16.4 culture supernatant at 4 C. for 60 min. Sheep anti-mouse immunoglobulin (1 ul; Cappel) is added to each sample and incubation continued for 30 min. Immune complexes are pelleted using fixed Protein A-bearing *Staphylococcus aureus* and washed. Samples are analyzed by SDS-polyacrylamide gel electrophoresis in 7.5% acrylamide—0.17% bis-acrylamide gels. The gels are treated for fluorography and exposed to preflashed Kodak X-Omat AR film for 10 days.

Anchorage-Independent Growth Assays and Results

Anchorage independent growth as assessed by determining the colony-forming efficiency of cells suspended in soft agar. Assays are conducted using 60 mm tissue culture dishes containing a 6 ml free feeder layer and a 1 ml top layer in which the cells are suspended. Feeder layers consist of 0.24% agarose RPMI-1640 supplemented with 10% fetal calf serum, 2 mM L-glutamine, and antibiotics. When antibody is added to soft agar cultures, it is incorporated into the top layer only. Cultures are fed after 7 days with 1 ml of DMEM containing 10% fetal calf serum and antibiotics, and the same amount of antibody that was added on day 1. On day 13, the cultures are fed 1 ml of HBSS containing 1 mg/ml p-iodonitrotetrasolium violet (INT, Sigma) to stain colonies. The next day colonies >0.5 mm are counted using a dissecting microscope and a calibrated template. Each group represents the mean of triplicate samples.

One of the most stringent characteristics distinguishing malignant from non-malignant cells is the capacity for anchorage-independent growth. Exposure of neu-transformed cells to the p185 specific monoclonal antibody 7.16.4 causes the down-modulation of p185 from the cell surface and results in loss of the capacity for anchorage-independent growth. The ability of each of the p185 specific antibodies to inhibit the anchorage-independent growth of neu-transformed cells is shown in Table 1. As shown in Table 1 below, all of the anti-p185 monoclonal antibodies are able to cause over fifty percent inhibition of the anchorage-independent growth of B104-1-1 cells at doses of less that 1 ug per dish. The potency of the different anti-p185 antibodies in inhibiting anchorage-independent growth parallels their relative affinity for binding B104-1-1 cells, with antibody 7.16.4 having the highest affinity and antibody 7.21.2 having the lowest affinity. The relative affinity is deduced by the saturable binding curves of the various purified antibodies for p185 expressed on B104-1-1 cells. In addition, the antibodies identify three distinct domains of p185. Thus, 7.16.4, 7.9.5, and 7.21.2 react with independent epitopes of the extra cytoplasmic portions of p185. Hence, the effects observed can not be attributed to the binding of the different monoclonals to the same site.

TABLE I

Anti-p185 Monoclonal Antibodies Inhibit
The Anchorage-Independent Growth Of neu-transformed Cells

| Antibody | (specificity) | Anchorage-Independent colonies[a] (percent inhibition) | | | | |
|---|---|---|---|---|---|---|
| | | 0 | 100 ng | 1 ug | 10 ug | 100 ug |
| None | | 25 ± 2.2 | | | | |
| 7.5.5 | (anti-p185) | | 15 ± 0.3 (40) | 10 ± 2.5 (60) | 6 ± 1.0 (76) | 4 ± 0.9 (84) |
| 7.9.5 | (anti-p185) | | 14 ± 1.2 | 9 ± 0.9 | 7 ± 0.6 | 0.3 ± 0.3 |

TABLE I-continued

Anti-p185 Monoclonal Antibodies Inhibit
The Anchorage-Independent Growth Of neu-transformed Cells

| Antibody | (specificity) | Anchorage-Independent colonies[a] (percent inhibition) | | | | |
|---|---|---|---|---|---|---|
| | | 0 | 100 ng | 1 ug | 10 ug | 100 ug |
| 7.16.4 | (anti-p185) | | (44)<br>3 ± 3.3 | (64)<br>1 ± 0.6 | (72)<br>1 ± 0.6 | (99)<br>0.7 ± 0.3 |
| 7.16.4 | (anti-p185) | | (88)<br>16 ± 1.9 | (96)<br>3 ± 0.9 | (96)<br>1 ± 0.3 | (97)<br>0.3 ± 0.3 |
| 7.21.2 | (anti-p185) | | (36)<br>25 ± 2.0 | (88)<br>11 ± 0.9 | (96)<br>12 ± 1.9 | (99)<br>12 ± 1.2 |
| 9BG5 | (IgG2a, anti-reovirus) | | (0)<br>21 ± 1.5 | (56)<br>23 ± 2.0 | (52)<br>21 ± 3.2 | (52)<br>22 ± 1.3 |
| 87.92.6 | (IgM, anti-beta andrenergic receptor) | | (16)<br>22 ± 1.2<br>(12) | (8)<br>26 ± 2.6<br>(<0) | (16)<br>29 ± 2.9<br>(<0) (8) | (12)<br>23 ± 1.2 |

[a]colonies > 0.5 mm were counted using a dissecting microscope after 14 days, described in Materials and Methods.

In contrast to the effects of anti-p185 antibodies, two control monoclonal antibodies fail to significantly inhibit the anchorage-independent growth of neu-transformed cells even at 100 ug per dish (Table I). It is important to note that one of these control antibodies, 87.92.6, is reactive with a beta-adrenergic like receptor on B104-1-1 cells and shows significant binding to these cells by immunofluorescence, but has no effect on their anchorage-independent growth. This demonstrates that the effects of the anti-p185 monoclonal antibodies on the anchorage-independent growth of neu-transformed cells does not simply result from antibody binding the cell surface, but reflects a specific cytostatic effect resulting from antibody binding to specific domains of the p185 molecule.

The ability of anti-p185 monoclonal antibodies to inhibit the growth of neu-transformed cells occurs exclusively under conditions that are selective for neoplastic behavior, such as when the cells are suspended in soft agar.

Effect of Anti-p185 Monoclonal Antibodies on Adherent Growth in Ten Percent Fetal Calf Serum Adherent growth in ten percent fetal calf serum, which is a property shared by non-neoplastic cells as well as neoplastic cells, is unaffected by anti-p185 antibodies. Antibody 7.16.4 has no effect on the adherent growth of neu-transformed cells in liquid medium, even at concentrations that inhibit the anchorage-independent growth of neu-transformed cells by >95%. Because the expression of p185 is not significantly affected when cells are grown under varying conditions, differential expression patterns of p185 is not considered a significant element in the failure to observe affects of anti-p185 antibodies on cells grown in liquid 27 media. Collectively, these studies demonstrate that anti-p185 antibodies selectively inhibit the neoplastic behavior of neu-transformed cells, without in any way affecting cell viability.

Effect of Anti-p185 Antibody on Rats

Intravenous injection of up to 4mg of purified antibody 7.16.4 per rat has no discernable toxic effects on BDIX rats or on the offspring of BDIX rats when given on day 16 of pregnancy in toxicity studies.

Antibody Dependent Complement-Mediated Cytotoxicity Assays

Tumor targets are removed from culture dishes and incubated in a volume of 0.5 ml with 200 uCi of Na$^{51}$CrO$_4$ (New England Nuclear) at 37 C. for 60 minutes. The cells are then washed three times in Hank's Balanced Salt Solution (HBSS), counted in a hemocytometer, and diluted to $10^5$ cells per ml. 100 ul of cell suspension ($10^4$) cells) is added to wells of a 96 well microtiter plate. 50 ul of appropriately diluted rabbit complement is added to each well. Next, 50 ul aliquots containing the appropriate amounts of purified monoclonal antibodies are added to each well. Appropriate control wells containing cells alone, cells plus antibody only, cells plus complement only and cells plus Triton x-100 detergent ( to effect maximal cell lysis) are set up in parallel. Microtiter plates are incubated at 37 C. for 1 hr and then centrifuged at 1000×g for 10 minutes. 100 ul of supernatant is collected from each well, and $^{51}$Cr released into the supernatant is assayed in a gamma counter. Specific release is calculated from the formula: x-C/M-C, where x represents the $^{51}$Cr activity in counts per minute of the experimental wells, C represents the $^{51}$Cr activity of the complement control wells, and M represents the maximal $^{51}$Cr activity released from detergent containing wells. Release from wells containing antibody without complement is never significantly greater that the release from wells containing medium only. All experimental groups represent the mean of triplicate samples. Individual samples never varied from the mean by more than 10%.

All of the anti-p185 antibodies (7.5.5, 7.9.5, 7.17.4, 7.16.5, and 7.21.2) exert a cytostatic effect on the growth of neu-transformed cells suspended in soft agar. In order to identify additional mechanisms by which anti-p185 monoclonal antibodies might exert anti-tumor effects, we examined their abilities to kill tumor cells in vitro in the presence of rabbit complement. Purified immunoglobulin from the 6.16.4 hybridoma is able to lyse neu-transformed cells in the presence of complement in a one hour $^{51}$Cr release assay at immunoglobulin concentrations as low as 5 ng/ml. The ability of antibody 7.16.4 to kill neu-transformed cells is completely dependent on the addition of complement since purified immunoglobulin does not exert cytotoxic effects in the absence of complement in either short term in vitro $^{51}$Cr release assays or longer term cell cultures. The anti-p185 antibodies, 7.5.5 and 7.16.5 are also able to cause significant lysis of the neu-transformed NIH3T3 cell line B104-1-1 in the presence of complement. There is no killing of the control cell line XHT-1-1a by any of the monoclonal anti-p185 antibodies.

Antibody Dependent Cell-Mediated Cytotoxicity Assays

Tumor targets are labeled with Na$^{51}$CrO$_4$ as described above. 1×10$^4$ labeled tumor cells, 20 ug of antibody 7.16.4, and varying numbers of effector cells are cultured in DMEM supplemented with 10% fetal calf serum and antibiotics in wells of 96 well microtiter plates in a total volume of 200 ul. The plates are incubated at 37 C. in a humidified 5% $CO_2$ incubator for 24 hours. After this time the plates are spun at 1000×g and $^{51}CrO_4$ release is assayed as described above. Control wells containing tumor cells alone, tumor cells plus spleen cells alone, tumor cells plus antibody alone, and tumor cells plus Triton x-100 (to effect maximal release) are set up in parallel with the experimental wells. Specific release is calculated according to the formula: x-C/M-C, where x represents the $^{51}Cr$ activity of the effector cell control wells, and M represents the maximal $^{51}Cr$ activity released from the detergent containing wells. Release from wells containing tumor cells and antibody without effector cells is never significantly greater than the release from wells containing medium only. All experimental groups represent the mean of triplicate samples. Individual samples never varied from the mean by more than 10%.

In contrast to the effective complement-mediated lysis observed with several of the anti-p185 monoclonal antibodies, only the IgG2a anti-185 antibody 7.16.4 is able to mediate even modest levels of antibody-dependent cell-mediated lysis of neu transformed cells (Table III). Anti-p185 antibodies of other isotypes have no activity in ADCC assays. The level of cell killing obtained with antibody 7.16.4 is relatively low regardless of whether spleen cells, complete with Freund's adjuvant elicited macrophages or thioglycollate elicited macrophages are used as cellular effectors. Even enhancing the adherence of anti-p185 antibodies to the surface of effector cells with polyethylene glycol, a procedure that increases ADCC activity, fails to increase the cell-mediated lysis of neu-transformed cell lines with the same result. Therefore, we conclude, ADCC is not an important effector mechanism in this system.

Competitive Binding Studies

Monoclonal antibodies are covalently coupled with $^{125}I$ (as carrier free $Na^{125}I$, New England Nuclear) to a specific activity of 500–2500 CPM/ng using chloramine according to the method of Hudson et al. in *Practical Immunology* (Blackwell Scientific Publications, Oxford, 1980), p. 240, which is specifically incorporated herein. Competition experiments are conducted by incubating 1×10$^6$ B104-1-1 cells with labeled antibody (at about 75% of the saturating concentration) and varying amounts of unlabeled antibody in 200 ul of radioimmunoassay (RIA) buffer (HBSS plus 5% fetal calf serum and 0.2% sodium azide) for 4 hours at 4 C. The cells are washed three times in 2.0 ml of chilled RIA buffer by centrifugation, and the bound radioactivity is measured in a gamma counter. All samples are performed in duplicate; there was less than a 10% difference in iodinated antibody binding by replicate samples.

Unlabeled antibody 7.16.4 is able to compete with iodinated antibody 7.16.4 for binding to p185 on the surfaces of neu-transformed cells, whereas none of the other anti-p185 antibodies show significant competition. This could either be due to these other antibodies binding domains of the p185 molecule that are spatially distinct from that bound by antibody 7.16.4, or to their binding the same domain with a much less affinity. Antibodies 7.5.5, 7.9.5, and 7.16.5 are all able to compete with iodinated antibody 7.9.5 for binding p185, whereas antibodies 7.16.4 and 7.21.2 do not inhibit the binding of antibody 7.9.5. This demonstrates that antibody 7.9.5, 7.5.5 and 7.16.5 bind the same antigenic domain, which is distinct from that bound by antibody 7.16.4. Furthermore, iodinated antibody 7.21.2 can be inhibited in its binding of any of the other anti-p185 antibodies, and is not inhibited by any of the other anti-p185 antibodies, thus it defines yet a third antigenic domain.

III. Tumor Cell Implantation and Measurement of Tumor Growth

Tumor cells are released from tissue culture dishes with trypsin/Versene and washed three times in HBSS. Viable tumor cells (1×10$^6$) are then injected subcutaneously in the mid-dorsum of nude mice. Growing tumors are measured with Vernier calipers on the days indicated, and tumor size is calculated as the product of tumor length and width, a method that has been shown to correlate with tumor weight. Data are presented as the mean +−S.E.M. Significance is determined by comparing the means of different groups using Student's t test.

Complement and Macrophage Depletion in vivo

Complement is depleted by multiple intravenous injections of cobra venom factor (Sigma) according to the method of Pepys, "Role of Complement in induction of the allergic response." Nature New Biology 237: 157 (1972) which is specifically incorporated herein. Nude mice receive 1 unit of cobra venom factor diluted in HBSS every 8 hours for a total of 4 doses beginning 40 hours before tumor cell implantation and another 4 doses 48 hours after tumor cell implantation. Macrophage functions are inhibited by intravenous injection of lambda carrageenan (Sigma) according to the procedure of Yung and Cudkowicz, "Abrogation of resistance to foreign bone marrow grafts by carageenans II. Studies with the anti-macrophage agents." J. Immunology 119: 1310 (1977), which is specifically incorporated herein. Nude mice receive 0.5 mg of carrageenan diluted in HBSS 48 hours preceding and 48 hours following tumor cell implantation.

Effects of Monoclonal Antibodies Binding to Separate Sites of neu Oncogene Encoded p185 Molecule in vivo FIG. 1 demonstrates that the intravenous administration of anti-p185 monoclonal antibodies of several IgG subclasses results in substantial inhibition of the tumorigenic growth of neu-transformed cells. The IgG1 monoclonal antibodies 7.9.5 and 7.21.2 (panels 1B and 1E), the IgG2a monoclonal antibody 7.16.4 (panel 1C), and the IgG2b monoclonal antibody 7.5.5 (panel 1A), all of which are reactive with the p185 molecule, were able to inhibit the tumorigenic growth of neu-transformed cells by 70–95 percent (p, 0.05 at all days measured). Neither the control IgG2a monoclonal antibody UPC 10 (panel 1F) nor the IgM anti-p185 monoclonal antibody 7.16.5 (panel 1D) had any significant effect on B104-1-1 tumor growth. Although tumor growth was inhibited and the survival of tumor-bearing mice was extended by anti-p185 antibody treatment, all animals eventually developed lethal tumors. Extensive studies of individual antibody treatment at a variety of doses and treatment schedules, involving several hundred animals, failed to produce a single cure.

As shown in Table 2, treatment of mice injected with 1×10$^6$ B104-1-1 cells, using mixtures of antibodies specific for two distinct antigenic domains of p185, resulted in complete tumor eradication in approximately half of the treated animals. In contrast treatment with individual antibodies in identical or higher total immunoglobulin doses failed to eradicate tumors in any animals. Thus the enhanced anti-tumor effect of antibody mixtures represents true herapeutic synergy. Interpreting these results in light of he data in Table 3 suggest that the reduction in tumor incidence following treatment with synergistic antibody mixtures corresponds to a reduction in the initial tumor inoculum for $1 \times 10^6$ cells to less than $1 \times 10^4$ cells, or a greater than 99% decrease in tumor burden.

TABLE 2

Synergistic Anti-Tumor Effects of Monoclonal Antibodies Reactive With Distinct Domains of p185

| Antibody Treatment[a] | # Sites on p185 Bound | Fraction Cured of Tumors[b] | | |
|---|---|---|---|---|
| | | Exp. 1 | Exp. 2 | Total |
| None | — | 0/5 | 0/18 | 0/23 |
| 7.5.5 | 1 | 0/5 | — | 0/5 |
| 7.9.5 | 1 | 0/5 | 0/6 | 0/11 |
| 7.16.4 | 1 | 0/5 | 0/6 | 0/11 |
| 7.5.5 + 7.16.4 | 2 | 1/5 | — | 1/5 |
| 7.9.5 + 7.16.4 | 2 | 2/5 | 7/12 | 9/17 |
| 7.5.5 + 7.9.5 | 1 | 0/5 | — | 0/5 |

[a]Balb/c nude mice were injected subcutaneously in the mid-dorsum with 1 × $10^6$ B104-1-1 tumor cells. Intravenous antibody treatment with 50 ug (Exp1) and 100 ug of total immunoglobulin (Exp 2) was carried out shortly after tumor implantation, and was repeated twice weekly for two weeks.
[b]Mice were examined twice weekly for the development of tumors. Animals were considered cured if they failed to develop tumors 60 days after the cessation of antibody treatment.

TABLE 3

Tumorigenicity of B104-1-1 Tumor Cells in Nude Mice

| Tumor Cell Inoculum[a] | Mice with Tumors[b]/ Mice Injected | Tumors Detectable (Days) |
|---|---|---|
| $1 \times 10^6$ | 12/12 | 3 |
| $1 \times 10^5$ | 12/12 | 8 |
| $1 \times 10^4$ | 4/6 | 19 |
| $1 \times 10^3$ | 2/6 | 26 |
| $1 \times 10^2$ | 1/6 | 30 |
| $1 \times 10^1$ | 0/6 | — |

[a]Balb/c nude mice were injected subcutaneously in the mid-dorsum with the indicated number of B104-1-1 tumor cells in a total volume of 0.1 ml.
[b]Mice were examined three times a week for the development of tumors. All tumors appeared within 30 days of tumor cell injection; there was no subsequent appearance of tumors during an observance of tumors during an observation period extending an additional 60 days.

Figure 2:
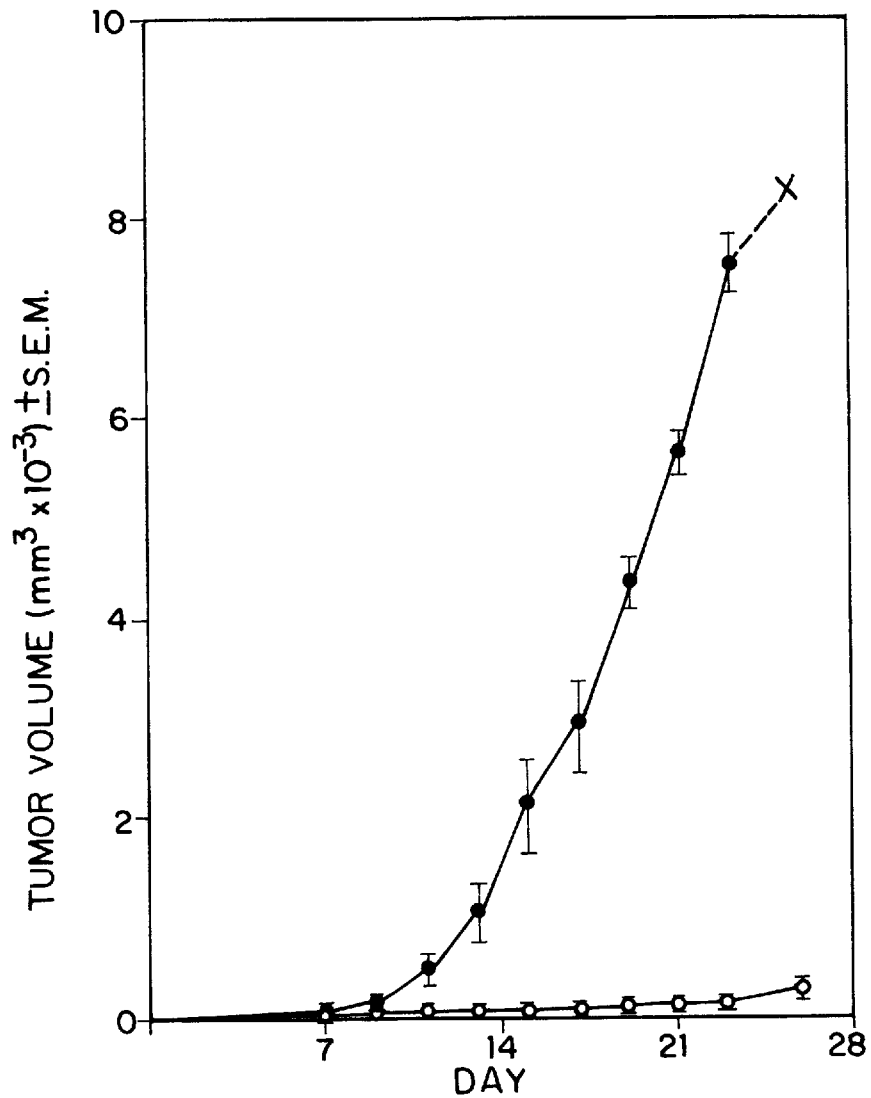
FIG. 2 shows the effects of anti-p185 antibody treatment of tumor-bearing mice.

As shown in FIG. 2, anti-p185 antibody treatment of tumor-bearing mice beginning seven days after tumor implantation was able to almost completely inhibit subsequent tumor growth (open circles). In contrast, untreated animals rapidly developed large tumors that resulted in their deaths within 25 days (FIG. 2, closed circles).

However, although anti-p185 antibody treatment resulted in almost complete inhibition of tumor growth, established tumors were not eradicated. After antibody treatment was stopped the tumors began growing again, resulting in the eventual deaths of all treated animals. Thus anti-p185 antibody treatment significantly extended the survival of animals with established tumors, but was not curative. The inability of combination antibody treatment to eradicate established tumors most likely reflects tumor size.

Established tumors measured 70 mm$^3$ when treatment was initiated, representing about $2 \times 10^7$ cells. Tumors of this size may exceed the ability of anti-p185 antibody treatment (at doses tested) to cause complete tumor regression.

IV. Immunohistochemical Localization of p185 in Developing Rat Tissues

Frozen tissues were obtained from E14 embryos (embryonic day 14) or PND-1 rats (post natal day one) (intestine and skin tissue were used). Frozen sections (i.e., tissue portions) were mounted on poly-L-lysine-coated glass microscope slides and fixed with 1% paraformaldehyde in PBS for 5 minutes at 4 C. Subsequent washes and incubations were performed in PBS plus 1% fetal bovine serum at room temperature. The sections were incubated for 30 minutes with a saturating concentration of primary antibody. The primary antibody was 7.16.4 antibody specific for p185. Bound primary antibodies were labeled using biotinylated horse anti-mouse IgG (Vector Laboratories) and streptavidin-biotinylated-peroxidase (Zymed Laboratories) using the procedure of Thiery et al., Develop. Biol. 93: 324–343, (1982), which is specifically incorporated herein, and according to the manufacturer's instructions except that the horse anti-mouse serum was depleted of reactivity with rat IgG by passage over a column containing rat IgG covalently linked to Ultrogel AC34 (LKB Instruments). The peroxidase substrate was chromogenic and consisted of 1 mg/ml 3,3'-diaminobenzidine, 0.03% $H_2O_2$, and 5 mM imidazole, as color enhancer. The sections were stained according to the procedure of Trojanowski et al., J. Histochem. Cytochem 31: 1217–1223, (1983), which is specifically incorporated herein. The sections were counterstained with methyl green. In transverse section of the E14 embryo, prominent staining for p185 could be seen in the developing dorsal root ganglion and mesenchymal tissue. In the post natal day one rat, strong immunoreactivity could be seen in intestinal villus epithelium and in the basal layer of skin. Faint staining could also be seen in the underlying connective tissue.

V. Autoradiographical Detection of Expression of the neu Oncogene in Fetal Rat Tissues Total tissue RNA was prepared from whole embryos at E14, E16, E18 and from individual organs of E18 embryos and older animals. Fetal ages were estimated from the probable time of impregnation of the mothers and confirmed by morphological criteria following the procedure of Long and Burlingame, University of California Publications in Zoology, 43: 143–183, (1938), and by measurement of the crown-rump length following the procedure of Maniatis et al., Molecular Cloning: A Laboratory Manual, (Cold Spring Harbor Laboratory, New York, 1982). RNA was prepared by the guanidine isothiocyanate-cesium chloride method following the procedure of Hung et al. , Proc. Nat'l Acad. Sci. U.S.A. 83: 261–264, (1986), which is specifically incorporated herein. 20 ug of RNA per lane was electrophoresed in a 1% agarose/2.2M formaldehyde gel and transferred to a nylon membrane (Gene Screen Plus, NEN Products, DuPont company) according to the manufacturers instructions. The membranes were hybridized for 18 hours at 42 C. in the presence of 50% formamide, 10% dextran sulfate, 1M NaCl, and 1% SDS. A DNA fragment, a 420 bp BamH1 fragment of a neu oncogene cDNA, labeled by random primer extension to a specific activity of $5 \times 10^8$ cpm/ugm was used as a probe for neu. The probe was prepared according to the procedure of Bargmann et al. Nature 319: 226–230, (1986), which is specifically incorporated herein. The mouse actin probe contained mouse actin cDNA subcloned into Pst 1 site of pBR322. It was a gift and was prepared by the procedure of Spiegelman and Green and was labeled with nick translation kit (Bethesda Research Laboratories, Bethesda, Md.) to a specific activity of $1 \times 10^8$ cpm/ug. After hybridization, the membranes were washed in 2×SSC (1×SSC is 0.15M NaCl, 0.015M Na-Citrate) for 15 minutes at room temperature and twice in 1×SSC, 1% SDS for 30 minutes at 60 C. The membranes were then exposed to XAR-5 x-ray film (Kodak) using an intensifying screen for 12 days for neu or 6 hours for actin at −70 C.

The level of neu mRNA, indicating the activation of the neu gene was highest at embryonic day 14 (E14). Expression was decreased significantly by E18. In spite of the decrease of the expression level in RNA prepared from whole embryos, a high level of expression was apparent in the lung, intestine and kidney of E18 embryos, with lower levels in skin. Lower levels of mRNA persisted in these tissues in newborn, weanlings and adult animals. To ensure that the quantitative differences in neu gene expression were real, the blots were washed and rehybridized with a probe for cytoplasmic actin according to the procedure of Spiegelman et al., J. Biol. Chem. 258: 10083–10089, (1983), which is specifically incorporated herein, which has been shown to be expressed at a nearly constant level throughout development. Results with this probe showed that the differences in neu gene expression are accurate and not due to experimental procedure.

VI. Antibodies Specific for Human neu Oncogene

Rat and human neu oncogene DNA sequences are similar and the two genes share some sequences as can be shown by computer-aided analysis of the structure of the genes. Antibodies to the human gene can be produced by following the procedure as set forth above for making antibodies to the rat neu oncogene and using the rat neu oncogene sequences which are shared with human neu oncogene instead of the rat neu oncogene.

Anti-Tumor Activity of Combinations of Antibodies Binding to Different Domains of p185

Pairs of monoclonal antibodies binding to different domains or epitopes of p185 were tested for their ability to inhibit tumor growth. The monoclonal antibodies were produced as described herein. Antibodies were subjected to competitive binding studies, as described herein, to determine which domain the antibodies bind in relation to the others. The antibodies were also isotyped as described herein. Once the relative binding domains were determined, antibodies from different groups were paired and tested for their ability to inhibit tumor growth using the method previously described herein. Ten mice were tested in each group, and each mouse received a total of 100 μg of immunoglobulin.

As a result of competitive binding studies, antibody 7.16.4 was found to bind to domain 1, antibodies 7.5.5, 7.9.5 and A11 were found to bind to domain 2, and antibody 7.21.2 was found to bind to domain 3. The denominations of domains 1, 2, and 3 are arbitrary and are used as a short hand to group antibodies that competitively bind to p185 into the same group. Antibodies placed into any one group competitively bind with other antibodies of the same group to p185, but do not to any substantial extent inhibit binding of antibodies to other portions of p185.

Isotype analysis of the antibodies provided the following isotypes for the antibodies: IgG1—antibody 7.9.5; IgG2a—antibodies A11 and 7.16.4; IgG2B—antibody 7.5.5; and IgG1—antibody 7.21.2.

As shown in Table 4, combinations of antibodies binding to different domains of p185 were able to significantly reduce tumor size.

TABLE 4

SYNERGISTIC AND EFFECT ANTI-TUMOR THERAPY

| Antibody Pair | Cure of Tumor | Reduced Tumor Growth Compared to Either Antibody At Day 7 |
| --- | --- | --- |
| 1) 7.5.5 + 7.16.4 | 2/10 (~20%) | 60% |
| 2) A11 + 7.16.4 | 8/10 (~80%) | >80% |
| 3) 7.16.4 + 7.21.2 | 0/10 (0%) | 30% |
| 4) 7.9.5 + 7.21.2 | 0/10 (0%) | 20% |

As shown in Table 4, the combination of antibodies 7.5.5 and 7.16.4, which bind to domains 2 and 1 respectively, was able to cure approximately 20 of the tumors and reduced tumor growth by sixty per cent when compared to tumor growth reduction produced by either antibody at day 7; i.e. the combination of antibodies produced an additional sixty per cent tumor reduction when compared to the amount of tumor reduction produced by either antibody alone. The combination of antibodies A11 and 7.16.4, which bind to domains 2 and 1 respectively, was able to cure approximately 80% of the tumors and reduced tumor growth by more than eighty percent. The combination of antibodies 7.16.4 and 7.21.2, which bind to domains 1 and 3 resepctively, did not cure any of the tumors, but did reduce tumor growth by thirty per cent. Likewise, the combination of antibodies 7.9.5 and 7.21.2, which bind to domains 1 and 3 respectively, did not cure any of the tumors, but did reduce tumor growth by twenty percent.

Hybridoma cell line producing monoclonal antibody 7.9.5 was deposited in the American Type Culture Collection, 12301 Parklawn Drive Rockville, Md. 20852-1776 on Jul. 3, 1990 and has accession number HB10492. Hybridoma cell line producing monoclonal antibody 7.16.4 was deposited in the American Type Culture Collection on Jul. 3, 1990 and has accession number HB10493.

We claim:

1. A method of treating mammalian cancer tumors having cells which express p185 the translation product of the neu oncogene on their surfaces, comprising the steps of:
   a) providing a first antibody specific for a first epitope on an extracellular domain of said translation product;
   b) providing a second antibody specific for a second epitope on an extracellular domain of said translation product, the combination of said first and second antibodies being selected to produce synergistic inhibition of tumor growth; and
   c) contacting said cells with said first and second antibodies under conditions which allow said first and second antibodies to bind to said translation product on the surfaces of said cells to a degree sufficient to inhibit the growth of the tumor.

2. The method of claim 1 wherein said first antibody is monoclonal antibody 7.16.4.

3. The method of claim 1 wherein said second antibody is monoclonal antibody 7.9.5.

4. The method of claim 1 wherein said first antibody and said second antibody are unlabelled.

5. The method of claim 4 wherein said is first antibody monoclonal antibody 7.16.4 and said second antibody is monoclonal antibody 7.9.5.

6. The method of claim 1 wherein:
   said first epitope is the epitope specifically recognized by monoclonal antibody 7.16.4; and
   said second epitope is the epitope specifically recognized by monoclonal antibody 7.9.5.

7. An injectable composition for treatment of a mammalian cancer tumor having cells which express p185 the translation product of the neu oncogene on the surfaces of the cells, comprising
   a) a first antibody specific to a first epitope on an extracellular domain of said translation product;
   b) a second antibody specific to a second epitope on an extracellular domain of said translation product the combination of said first and second antibodies being selected to produce synergistic inhibition of tumor growth; and
   c) a pharmaceutically acceptable injection vehicle.

8. The injectable composition of claim 7 wherein said first antibody is monoclonal antibody 7.16.4.

9. The injectable composition of claim 7 wherein said second antibody is monoclonal antibody 7.9.5.

10. The injectable composition of claim 7 wherein said first antibody and said second antibody are unlabelled.

11. The injectable composition of claim 10 wherein said is first antibody monoclonal antibody 7.16.4 and said second antibody is monoclonal antibody 7.9.5.

12. The injectable composition of claim 7 wherein:
   said first epitope is the epitope specifically recognized by monoclonal antibody 7.16.4; and
   said second epitope is the epitope specifically recognized by monoclonal antibody 7.9.5.

13. A method of treating mammalian cancer tumors having cells which express p185 the translation product of the neu oncogene on their surfaces, comprising the step of:
   injecting a mammal having such tumors, with an injectable composition consisting essentially of: a pharmaceutically acceptable injection vehicle, a first antibody specific for a first epitope on an extracellular domain of said translation product, and a second antibody specific for a second epitope on an extracellular domain of said translation product, the combination of said first and second antibodies being selected to produce synergistic inhibition of tumor growth.

14. The method of claim 13 wherein said first antibody is monoclonal antibody 7.16.4.

15. The method of claim 13 wherein said second antibody is monoclonal antibody 7.9.5.

16. The method of claim 13 wherein said first antibody and said second antibody are unlabelled.

17. The method of claim 16 wherein said is first antibody monoclonal antibody 7.16.4 and said second antibody is monoclonal antibody 7.9.5.

18. The method of claim 13 wherein:
   said first epitope is the epitope specifically recognized by monoclonal antibody 7.16.4; and
   said second epitope is the epitope specifically recognized by monoclonal antibody 7.9.5.

19. An injectable composition for treatment of a mammalian cancer tumor having cells which express p185 the translation product of the neu oncogene on the surfaces of the cells, consisting essentially of
   a) a first antibody specific to a first epitope on an extracellular domain of said translation product;
   b) a second antibody specific to a second epitope on an extracellular domain of said translation product the combination of said first and second antibodies being selected to produce synergistic inhibition of tumor growth; and
   c) a pharmaceutically acceptable injection vehicle.

20. The injectable composition of claim 19 wherein said first antibody is monoclonal antibody 7.16.4.

21. The injectable composition of claim 19 wherein said second antibody is monoclonal antibody 7.9.5.

22. The injectable composition of claim 19 wherein said first antibody and said second antibody are unlabelled.

23. The injectable composition of claim 22 wherein said is first antibody monoclonal antibody 7.16.4 and said second antibody is monoclonal antibody 7.9.5.

24. The injectable composition of claim 19 wherein:
   said first epitope is the epitope specifically recognized by monoclonal antibody 7.16.4; and
   said second epitope is the epitope specifically recognized by monoclonal antibody 7.9.5.

* * * * *

UNITED STATES PATENT AND TRADEMARK OFFICE
CERTIFICATE OF CORRECTION

PATENT NO. : 5,824,311
DATED : October 20,1998
INVENTOR(S) : Mark I. Greene et al It is certified that error appears in the above-identified patent and that said Letters Patent is hereby corrected as shown below:

Col. 12, line 67, "herea" should be -thera-

Col. 16, line 26, "resepctively" is misspelled. The correct spelling is -respectively-.

Signed and Sealed this

Fifteenth Day of June, 1999

Attest:

Q. TODD DICKINSON

*Attesting Officer*   Acting Commissioner of Patents and Trademarks